(12) United States Patent
Niddam-Hildesheim et al.

(10) Patent No.: US 7,582,759 B2
(45) Date of Patent: *Sep. 1, 2009

(54) DIASTEREOMERIC PURIFICATION OF ROSUVASTATIN

(75) Inventors: Valerie Niddam-Hildesheim, Kadima (IL); Natalia Shenkar, Petach Tiqva (IL); Kobi Chen, Ramat HaSharon (IL); Anna Balanov, Rehovot (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/520,296

(22) Filed: Sep. 12, 2006

(65) Prior Publication Data

US 2007/0191436 A1 Aug. 16, 2007

Related U.S. Application Data

(60) Provisional application No. 60/732,979, filed on Nov. 2, 2005, provisional application No. 60/723,491, filed on Oct. 3, 2005.

(51) Int. Cl.
*C07D 239/42* (2006.01)
(52) U.S. Cl. ..................................... 544/297
(58) Field of Classification Search ................... 544/297
See application file for complete search history.

(56) References Cited

U.S. PATENT DOCUMENTS

| 5,189,164 | A | 2/1993 | Kapa et al. |
| 5,218,138 | A | 6/1993 | Chiu et al. |
| 5,741,934 | A | 4/1998 | Sandler et al. |
| RE37,314 | E | 8/2001 | Hirai et al. |
| 6,437,065 | B1 | 8/2002 | Ritter et al. |
| 2005/0080134 | A1 | 4/2005 | Niddam-Hildesheim et al. |
| 2005/0159615 | A1* | 7/2005 | Lifshitz-Liron et al. ..... 560/179 |
| 2007/0179166 | A1* | 8/2007 | Niddam-Hildesheim et al. . 514/275 |

FOREIGN PATENT DOCUMENTS

| CN | 1 872 841 | 12/2006 |
| JP | 7118233 | 5/1995 |
| WO | WO 03/087112 A1 | 10/2003 |
| WO | WO 03/097614 A2 | 11/2003 |
| WO | WO 2005/040134 A1 | 5/2005 |
| WO | WO 2007/099561 | 9/2007 |

OTHER PUBLICATIONS

Szantay, et al., "Synthesis of Novel HMG-CoA Reductase Inhibitors, Naphthalene Analogs of Mevinolin", Liebigs Ann. Chem., 1992, pp. 145-157.
Ohrlein, et al., "Chemo-Enzymatic Approach to Statin Side-Chain Building Blocks", Adv. Synth. Catal., 2003, pp. 713-715, vol. 345.
Greene, "Protective Groups in Organic Synthesis", John Wiley & Sons, Inc., 1981.
Tetrahedron, 1997, pp. 10659-10670, vol. 53(31).
Scandinavian Simvastatin Survival Study Group, "Randomised Trial of Cholesterol Lowering in 4444 Patients With Coronary Heart Disease: The Scandinavian Survival Study (4s)", *The Lancet*, 1994, pp. 1383 - 1389, vol. 344.
Loubinoux, et al., "The Enantioselective Synthesis of Simplified Southern-Half Fragments of Soraphen A", Tetrahedron, 1995, pp. 3549-3558, vol. 51, No. 12.
Goodman and Gilman, The Pharmacological Basis of Therapeutics, p. 879 (9th Ed. 1996).
J.A.M.A. 1984, 251, 351-74.
Liming Shao, et al., Tetrahedron, vol. 49, No. 10,1997-2010 (1993).
JOC, 55, 5190-5192 (1990).
Journal of Labeled Compounds & Radiopharmaceuticals vol. XLI, pp. 1-7 (1988).
Reddy, G. Bhaskar, et al., Enantioselective Synthesis of β-Hydroxy δ-Lactones: A New Approach to the Synthetic Congeners of 3-Hydroxy-3-methylglutaryl Coenzyme A Reductase Inhibitors, J. Org. Chem., 1991, pp. 5752-5754, vol. 56.

* cited by examiner

*Primary Examiner*—Patricia L Morris
(74) *Attorney, Agent, or Firm*—Kenyon & Kenyon LLP

(57) ABSTRACT

The invention relates to diastereomerically pure rosuvastatin and processes for preparing diastereomerically pure rosuvastatin and its intermediates.

20 Claims, No Drawings

DIASTEREOMERIC PURIFICATION OF ROSUVASTATIN

RELATED APPLICATIONS

This application claims the benefit of provisional application Ser. No. 60/723,491, filed Oct. 3, 2005, and provisional application Ser. No. 60/732,979, filed Nov. 2, 2005, both of which are incorporated herein by reference.

FIELD OF INVENTION

The invention relates to an intermediate of rosuvastatin having low levels of diastereomeric impurities, and a process for the preparation thereof.

BACKGROUND OF THE INVENTION

Rosuvastatin calcium (monocalcium bis(+)7-[4-(4-fluorophenyl)-6-isopropyl-2-(N-methyl-N-methylsulfonylaminopyrimidin)-5-yl]-(3R,5S)-dihydroxy-(E)-6-heptenoate) is an HMG-CoA reductase inhibitor, developed by Shionogi for the once daily oral treatment of hyperlipidaemia (Ann Rep, Shionogi, 1996; Direct communications, Shionogi, 8 Feb. 1999 & 25 Feb. 2000). Rosuvastatin calcium is a superstatin, which can lower LDL-cholesterol and triglycerides more effectively than first generation drugs. Rosuvastatin calcium has the following chemical formula:

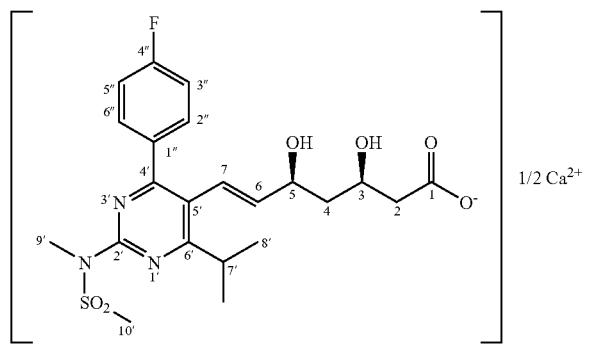

Rosuvastatin calcium is marketed under the name CRESTOR for treatment of a mammal such as a human. According to the maker of CRESTOR, it is administered in a daily dose of from about 5 mg to about 40 mg. For patients requiring less aggressive LDL-C reductions or who have pre-disposing factors for myopathy, a 5 mg dose is recommended, while 10 mg dose is recommended for the average patient, 20 mg dose for patients with marked hyper-cholesterolemia and aggressive lipid targets (>190 mg/dL), and the 40 mg dose for patients who have not been responsive to lower doses.

Rosuvastatin is an enantiomerically pure compound having two chiral centers at positions 3 and 5 of the molecule. Two of the four diastereoisomers of Rosuvastatin calcium are (3R,5R) and (3R,5S) derivatives. These diastereoisomers can be detected by reverse phase HPLC.

The synthetic process disclosed in US RE37,314E for rosuvastatin involves reduction of a keto-ester of a rosuvastatin at carbon 5 to obtain a diol ester. This reduction at position 5 is a standard typical step in the synthesis of statins. This reduction step however can result in diastereoisomeric impurities.

WO 2005/040134 discloses a process that is reported to reduce the diastereoisomer content of rosuvastatin through lactonization, or through conversion of amorphous rosuvastatin to crystalline rosuvastatin and subsequent conversion to the amorphous form.

There is a need in the art for preparation of diastereomerically pure rosuvastatin and its intermediates.

SUMMARY OF THE INVENTION

In one embodiment, the present invention provides a rosuvastatin intermediate of the following structure:

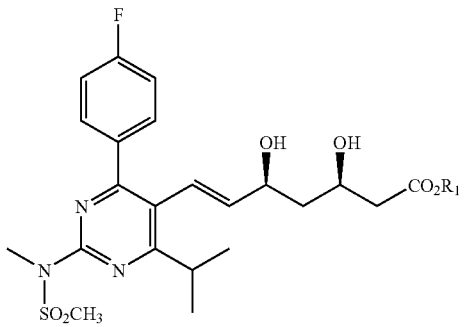

wherein $R_1$ is a $C_1$-$C_4$ alkyl group, having diastereomeric impurities of less than about 0.37%, as measured by area percentage HPLC.

In another embodiment, the present invention provides a process for preparing a rosuvastatin intermediate diol ester having the structure

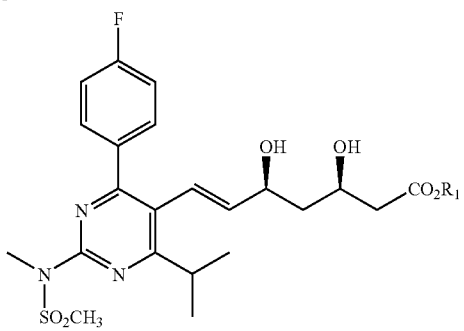

wherein $R_1$ is a $C_1$-$C_4$ alkyl group, comprising:

a) combining MeO-9-BBN with an organic solvent and a source of hydride ions;

b) adding to said combination a solution of a rosuvastatin keto-ester in an organic solvent, wherein the rosuvastatin keto-ester has the following formula:

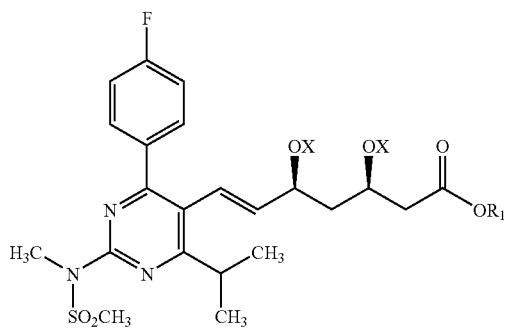

wherein X is hydrogen or forms a double bond to provide a ketone, with the proviso that at least one X forms a double bond, and $R_1$ is a carboxy protecting group, to obtain a reaction mixture; and c) maintaining the reaction mixture to obtain the diol ester.

In another embodiment, the present invention provides a one pot process for preparing rosuvastatin or a pharmaceutically acceptable salt thereof comprising:

a) combining MeO-9-BBN with an organic solvent and a source of hydride ions;

b) adding to said combination a solution of a rosuvastatin intermediate keto-ester in an organic solvent, wherein the rosuvastatin intermediate keto-ester has the following formula:

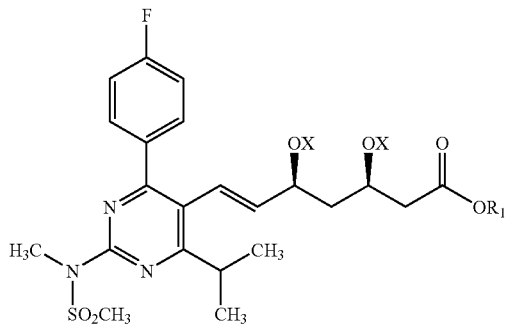

wherein X is hydrogen or forms a double bond to provide a ketone, with the proviso that at least one X forms a double bond, and $R_1$ is a carboxy protecting group to obtain a reaction mixture;

c) maintaining the reaction mixture to reduce the intermediate; and d) converting the reduced intermediate to rosuvastatin or a pharmaceutically acceptable salt thereof.

In another embodiment, the present invention provides a process for preparing an intermediate diol ester having the structure

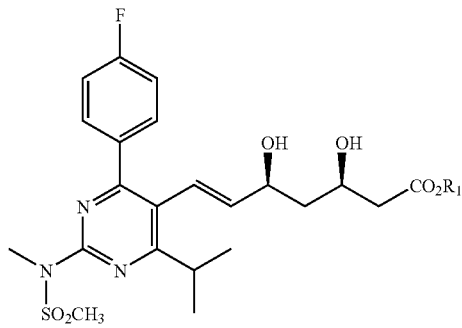

wherein $R_1$ is a carboxy protecting group comprising the steps of:

a) combining Diethylmethoxy borane (DEMB) with an organic solvent and a source of hydride ions;

b) adding to said combination a solution of a rosuvastatin keto-ester in an organic solvent, wherein the rosuvastatin keto-ester has the following formula:

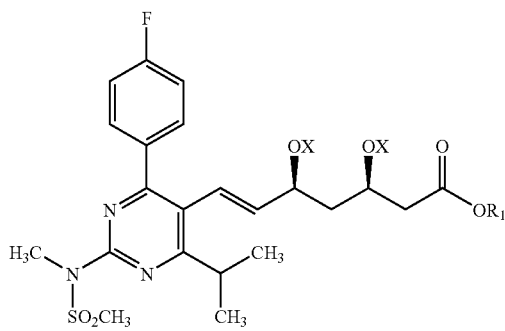

wherein X is hydrogen or forms a double bond to provide a ketone, with the proviso that at least one X forms a double bond, and $R_1$ is a carboxy protecting group, to obtain a reaction mixture wherein the total amount of the solvent from the keto ester-solution and the solvent that is combined with the DEMB is of about 30 to about 80 volumes (ml per gram of keto ester) in the reaction mixture; and c) maintaining the reaction mixture.

In another embodiment, the present invention provides a process for isolating a diol ester of rosuvastatin having the following structure:

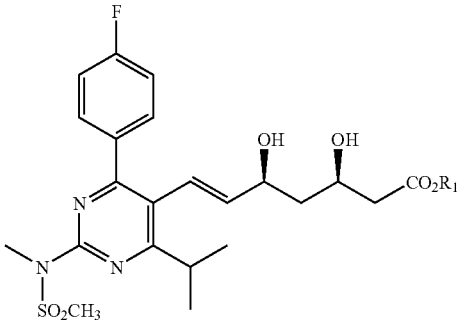

wherein $R_1$ is a carboxy protecting group, comprising crystallizing the diol ester from an organic solvent or a mixture of water and an organic solvent.

In another embodiment, the present invention provides a pharmaceutical composition comprising rosuvastatin or a pharmaceutically acceptable salt thereof prepared by converting $C_1$-$C_4$ rosuvastatin ester, preferably t-butyl ester, having less than about 0.3% diastereomeric impurities, as measured by area percentage HPLC, to rosuvastatin or a pharmaceutically acceptable salt thereof, and combining the rosuvastatin with a pharmaceutically acceptable excipient.

In another embodiment, the present invention provides use of $C_1$-$C_4$ rosuvastatin ester, preferably t-butyl ester, having less than about 0.3% diastereomeric impurities, as measured, by HPLC, in the manufacture of a pharmaceutical composition.

DETAILED DESCRIPTION OF THE INVENTION

Diastereomeric impurities in a composition of rosuvastatin may decrease the biological activity of the composition, and thus rosuvastatin having low levels of diastereomeric impurities is desirable for formulating pharmaceutical compositions of rosuvastatin. The invention provides a process of preparing rosuvastatin having low levels of diastereomeric impurities through the reduction of an intermediate $C_1$-$C_4$ ester of rosuvastatin, such as t-butyl rosuvastatin ester (TBRE), with 9-methoxy-9-bora-bicyclo[3.3.1]nonane ("MeO-9-BBN").

Reduction of a keto ester of rosuvastatin with MeO-9-BBN provides a diol ester of rosuvastatin having high diastereomeric purity. The diastereomeric purity of the diol ester can be further increased by crystallizing the diol ester from an organic solvent. The diastereomerically pure diol ester then can be used to prepare rosuvastatin and salts thereof also having low levels of diastereomeric impurities.

As used herein, the term "normal addition" generally refers to adding a reducing agent to a mixture of an ester to be reduced (see, e.g., US RE37,314E).

As used herein, the term "reverse addition" generally refers to adding a compound that is to be reduced, i.e., a keto-ester of rosuvastatin, to a mixture of a reducing agent (see, e.g., U.S. Pat. No. 5,189,164).

As used herein, the term "diastereomeric impurity" refers to the total amount of any diastereomer of rosuvastatin or its intermediates other than the preferred (3R,5S) diastereomer, and in particular refers to the (3R,5R) diastereoisomer of rosuvastatin or its intermediates.

As used herein, the term "diastereomerically pure TBRE", refers to TBRE having total diastereomeric impurities level of less than about 0.37% as measured by area percentage HPLC.

One embodiment of the invention provides a rosuvastatin intermediate having the following structure:

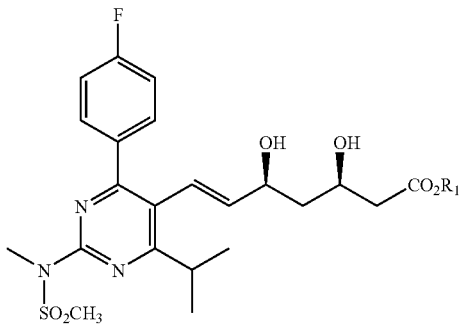

wherein $R_1$ is a carboxy protecting group.

Preferably, the intermediate is TBRE, having the following structure:

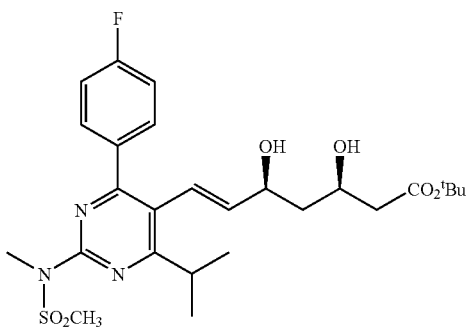

and having diastereomeric impurities of less than about 0.37%, more preferably less than about 0.13%, and most preferably less than about 0.11%, as measured by area percentage HPLC.

The invention provides a process for preparing rosuvastatin intermediate diol ester having the following structure

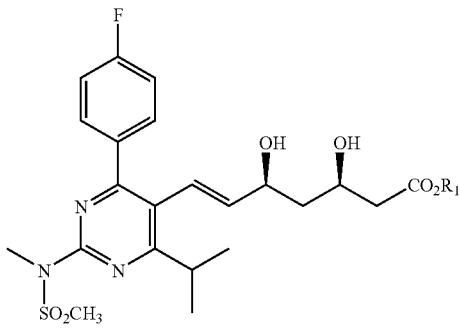

wherein $R_1$ is a carboxy protecting group, including a reverse addition process, wherein a keto-ester of rosuvastatin is added to a mixture of MeO-9-BBN and a reducing agent. The use of MeO-9-BBN as complexant in the reverse addition process of the invention allows for preferred stereoselective reduction and increased diastereomeric purity of the TBRE product.

The process includes the steps of: providing a solution of rosuvastatin keto-ester of the following formula:

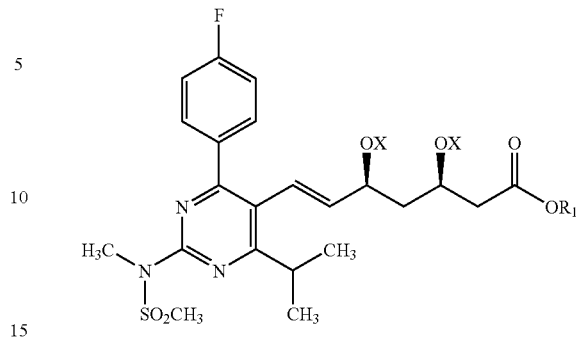

wherein X is hydrogen or forms a double bond to provide a ketone, with the proviso that at least one X forms a double bond, and $R_1$ is a carboxy protecting group, in an organic solvent; combining Methoxy-9-BBN with an organic solvent and a source of hydride ions; adding the solution of rosuvastatin keto-ester to the mixture of Methoxy-9-BBN to obtain a reaction mixture; and maintaining the reaction mixture to obtain an intermediate diol ester having the following structure:

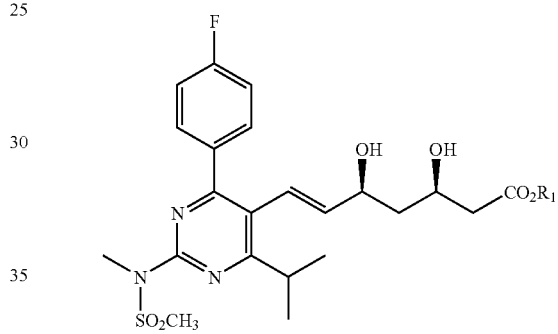

wherein $R_1$ is a carboxy protecting group. Preferably, $R_1$ is a $C_1$-$C_4$ alkyl group. More preferably, $R_1$ is t-butyl group (i.e., TBRE).

Preferably, the rosuvastatin keto-ester has a ketone on the fifth carbon (e.g., TB21). The structure of TB21 is shown below:

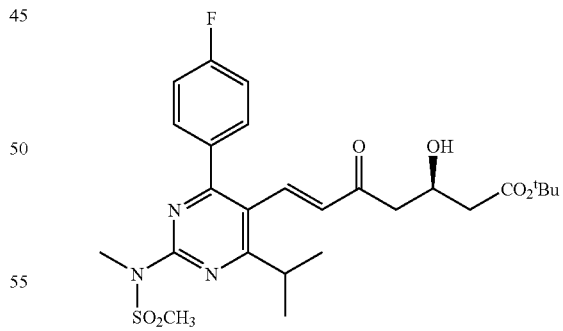

Preferably, the obtained diol ester has less than about 0.37% or less than about 0.30%, more preferably less than about 0.13%, most preferably, less than about 0.11% of diastereomeric impurities, as measured by area percentage HPLC.

Preferably, the solution of rosuvastatin keto-ester is prepared by combining the rosuvastatin keto-ester with a suitable organic solvent. A suitable organic solvent is a solvent which does not undergo a reduction in the presence of hydride ions. Preferably, the organic solvent is selected from the group consisting of: $C_1$ to $C_4$ alcohol, non-polar hydrocarbon solvent, $C_2$ to $C_8$ ether, chlorinated solvent, non-protic solvent and mixtures thereof. More preferably, the organic solvent is selected from the group consisting of: methylene chloride, toluene, methyl t-butyl ether, di-ethyl ether, tetrahydrofuran, dioxane, methanol, ethanol, isopropanol, and n-butanol. Most preferably, the solvent is a mixture of methanol and THF in a ratio of THF/MeOH of about 3.5/1, by volume per gram of the ester.

The mixture of Methoxy-9-BBN in organic solvent and a source of hydride ions is prepared by combining a source of hydride ions with Methoxy-9-BBN in a suitable organic solvent as provided above. Preferably, the source of hydride ions is selected from the group consisting of sodium borohydride, potassium borohydride, lithium borohydride, and sodium triacetoxy borohydride or selectride. More preferably, the hydride is sodium borohydride. Generally, about 1.5 to about 4 equivalents may be used per gram of keto-ester.

Preferably, the same solvent is used in preparing the mixture of Methoxy-9-BBN and hydride ions as is used in preparing the solution of rosuvastatin keto-ester. A mixture of tetrahydrofuran and methanol is a preferred solvent. Preferably, the mixture is cooled to a temperature of about −70° C. to about −80° C., more preferably, to a temperature of about −70° C.

The solution of rosuvastatin keto-ester is added to the mixture of Methoxy-9-BBN and hydride ions, providing a reaction mixture. Preferably, the keto-ester is added drop-wise. Preferably, the keto-ester is added over a period of time of at least about 30 minutes, more preferably about 1.5 to 2 hours.

Preferably, the solvent from the keto-ester solution and the solvent that is combined with the Methoxy-9-BBN are present in a total amount of about 30 to about 80 volumes (ml per gram of keto ester) in the reaction mixture.

Preferably, the solvent from the keto-ester solution makes up about 10% to about 40%, of the total amount of solvent in the reaction mixture, more preferably, about 15%.

Preferably, the reaction mixture is maintained, preferably while stirring, for a time sufficient to obtain rosuvastatin diol-ester. The reaction is almost immediate. Preferably, the reaction mixture is maintained for at least about 5 minutes, more preferably at least about 30 minutes, more preferably for at least about 0.5-3 hours.

Preferably, a quenching agent is combined with the reaction mixture to terminate the reaction. Preferably, the quenching agent is selected from the group consisting of: hydrogen peroxide, 3-chloroperbenzoic acid, ammonium chloride, aqueous solution of HCl, acetic acid, oxone, sodium hypochlorite, dimethyl disulfide, diethanolamine, hydroxylamine-O-sulfonic acid. More preferably, the quenching agent is hydrogen peroxide.

Another embodiment of the invention provides a process of preparing an intermediate diol ester having the following structure

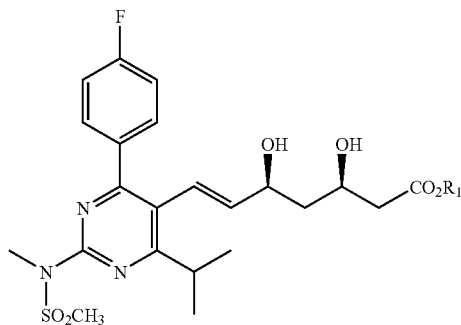

wherein $R_1$ is a carboxy protecting group, comprising the steps of: providing a solution of rosuvastatin keto-ester of the following formula:

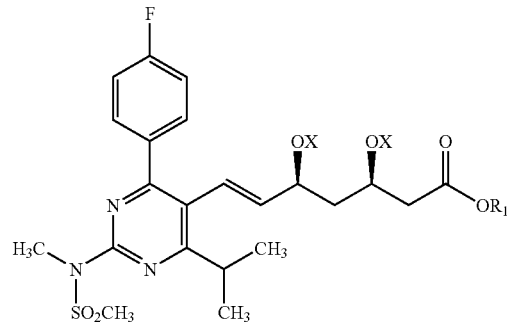

wherein X is hydrogen or forms a double bond to provide a ketone, with the proviso that at least one X forms a double bond, and $R_1$ is a carboxy protecting group, in an organic solvent; combining DEMB with an organic solvent and a source of hydride ions to obtain a mixture; adding the solution of rosuvastatin keto-ester to the mixture of DEMB to obtain a reaction mixture, wherein the total amount of the solvent from the keto ester-solution and the solvent that is combined with the DEMB is of about 30 to about 80 volumes (ml per gram of keto ester) in the reaction mixture; and maintaining the reaction mixture.

Preferably, $R_1$ is a $C_1$-$C_4$ alkyl group. More preferably, $R_1$ is t-butyl group (i.e., TBRE).

Preferably, the rosuvastatin keto-ester has a ketone on the fifth carbon (i.e., TB21). The structure of TB21 is shown below:

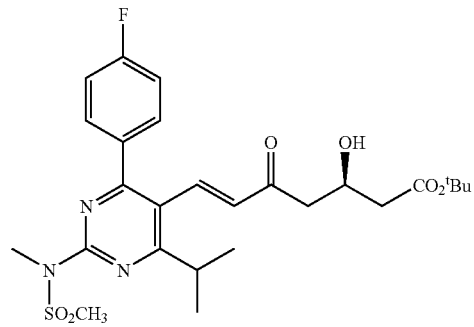

Preferably, the obtained diol ester has less than about 0.37%, more preferably less than about 0.13%, most preferably, less than about 0.11% of total diastereomeric impurities level, as measured by area percentage HPLC.

Preferably, the solution of rosuvastatin keto-ester is prepared by combining the rosuvastatin keto-ester with a suitable organic solvent. A suitable organic solvent is a solvent which does not undergo a reduction in the presence of hydride ions. Preferably, the organic solvent is selected from the group consisting of: $C_1$ to $C_4$ alcohol, non-polar hydrocarbon solvent, $C_2$ to $C_8$ ether, chlorinated solvent non-protic solvent and mixtures thereof. More preferably, the organic solvent is selected from the group consisting of: methylene chloride, toluene, methyl t-butyl ether, di-ethyl ether, isopropylether, tetrahydrofuran, dioxane, methanol, ethanol, isopropanol, and n-butanol. Most preferably, the solvent is a mixture of methanol and THF.

Preferably, the solvent from the keto-ester solution and the solvent that is combined with the DEMB are present in a total amount of about 30 to about 60 volumes (ml per gram of keto ester) in the reaction mixture.

Preferably, the source of hydride ions is selected from the group consisting of sodium borohydride, potassium borohydride, lithium borohydride, and sodium triacetoxy borohydride or selectride. More preferably, the hydride is sodium borohydride. Preferably, the source of hydride ions is present in an amount of about 1.5 to about 4 equivalents (per gram of keto ester), more preferably, about 2.7 equivalents (per gram of keto ester). Preferably, the solvent from the keto-ester solution makes up about 10% to about 40%, of the total amount of solvent in the reaction mixture.

Preferably, the same solvent is used in preparing the mixture of DEMB and hydride ions as is used in preparing the solution of rosuvastatin keto-ester. A mixture of tetrahydrofuran and methanol is a preferred solvent. Preferably, the mixture is cooled to a temperature of about −50° C. to about −80° C., more preferably, to a temperature of about −70° C.

The solution of rosuvastatin keto-ester is added to the mixture of DEMB and hydride ions, providing a reaction mixture. Preferably, the keto-ester is added drop-wise Preferably, the keto-ester is added over a period of time of at least about 30 minutes, more preferably about 1.5 to 2 hours.

Preferably, the reaction mixture is maintained, preferably while stirring, for a time sufficient to obtain rosuvastatin diol-ester. The reaction is almost immediate. Preferably, the reaction mixture is maintained for at least about 5 minutes, more preferably at least about 30 minutes, more preferably for about 0.5-3 hours.

Preferably, a quenching agent is combined with the reaction mixture to terminate the reaction. Preferably, the quenching agent is selected from the group consisting of: hydrogen peroxide, 3-chloroperbenzoic acid, ammonium chloride, aqueous solution of HCl, acetic acid, oxone, sodium hypochlorite, dimethyl disulfide, diethanolamine, acetone and hydroxylamine-O-sulfonic acid. More preferably, the quenching agent is hydrogen peroxide.

The following table summarizes the results obtained from the examples:

| Example | Addition Process | Complexant | Diastereoisomer impurites content (% area HPLC) |
| --- | --- | --- | --- |
| 1 | Reverse addition | DEMB | 8.89 |
| 2 | Reverse addition with 60 volumes | DEMB | 0.76 |
| 3 | Normal addition | DEMB | 0.64 |
| 4 | Reverse addition on 5 g | MeO-9-BBN | 0.11 |
| 5 | Reverse addition on 50 g | MeO-9-BBN | 0.13 |

The diol ester obtained may be recovered, or converted to rosuvastatin in one pot. Recovery may be carried out by evaporating the reaction mixture to obtain a residue.

Preferably, the diol ester is recovered by combining the reaction mixture with a mixture of water immiscible organic solvent and water; separating the organic phase from the two-phase system that forms; and removing the solvent.

The use of ammonium chloride during the work-up of the reaction is illustrated in Example 6. The use of ammonium chloride facilitates the dissolution of the salts formed after the quenching of the reaction with $H_2O_2$. The use of ammonium chloride allows the partial dissolution of the salts in the aqueous layer. The rest of the salts can then be removed by filtration. The washing with a mixture of water and brine allows the removal of the impurity octanediol, which forms after the quenching (decomplexation of OMe-9-BBN) of the reaction with $H_2O_2$. The $H_2O/NaCl$ ratio is preferably about 10/10 volumes in relation to TB21 or another ester. Preferably a second washing is carried out with a preferable ratio of about 10/2 volumes in relation to TB21 or another ester.

Preferably, the water immiscible organic solvent is selected from the group consisting of $C_4$ to $C_7$ esters and $C_6$ to $C_{10}$ aromatic hydrocarbons. Preferably, the solvent is selected from the group consisting of: ethyl acetate, toluene, methyl ethyl ketone, and mixtures thereof. More preferably, the solvent is ethyl acetate. The diol ester moves into the organic phase of the biphasic system, and the organic phase is separated, and then washed under basic and brine conditions, more preferably, with a mixture of saturated H2O/NaCl. The solvent may be removed by any technique known in the art, for example, by evaporation.

Another embodiment of the invention provides a process for increasing the diastereomeric purity of TBRE by crystallizing TBRE from a solution of the diol ester. In another embodiment the present invention provides a process for increasing the diastereomeric purity of TBRE by slurrying of the diol ester.

The process of crystallization of TBRE comprises the steps of: providing a solution of TBRE in a solvent selected from the group consisting of: $C_1$-$C_4$ alcohols, $C_3$-$C_8$ esters, $C_3$-$C_8$ ketones, $C_3$-$C_8$ ethers, $C_6$ to $C_{10}$ aromatic hydrocarbons, PGME (propylene glycol monomethyl ether), water, acetonitrile, and mixtures thereof; cooling the solution to crystallize the TBRE; and recovering the crystallized TBRE.

The process of slurrying TBRE comprises: combining TBRE with a solvent selected from the group consisting of: $C_1$-$C_4$ alcohols, $C_3$-$C_8$ esters, $C_3$-$C_8$ ketones, $C_3$-$C_8$ ethers, $C_6$ to $C_{10}$ aromatic hydrocarbons, PGME (propylene glycol monomethyl ether), water, acetonitrile, and mixtures thereof, to obtain a slurry; and recovering TBRE. Preferably, the recovery comprises filtering the slurry to obtain a precipitate. Preferably, the filtration is under reduced pressure. Preferably, the obtained precipitate is further dried.

Preferably, the solvent used in crystallization or slurry is selected from a group consisting of methanol, PGME, acetonitrile:water, acetone:water, acetone:MTBE (methyl tert-butyl ether), methanol:water, ethanol:water, ethanol:MTBE, acetonitrile:MTBE, methanol:MTBE, MEK (methyl ethyl ketone):MTBE and toluene. More preferably, the solvent is toluene, a mixture of methanol and water, or a mixture of acetonitrile and water. Most preferably, the solvent is toluene.

Preferably, crystallization or slurrying is performed with preferred solvents and solvent mixtures under conditions selected to increase purification. For example, crystallization with methanol is preferably carried out with about 3 volumes to about 10 volumes (ml per gram of TBRE) of MeOH. In one embodiment, the ratio of $MeOH:H_2O$ is preferably less than about 5:1 by volume. In another embodiment, ACN:MTBE or MeOH:MTBE with a ratio of less than about 2:10 by volume is used.

The crystallization or slurrying is typically carried out by heating the solution or slurry of TBRE to a temperature above about 50° C., followed by cooling. Cooling is preferably carried out to a temperature of about 40° C. to about 0° C., more preferably to a temperature of about 30° C. to about 0° C., and most preferably to about 5° C. to about 0° C.

A slurry may also be carried out by suspending the ester in an organic solvent at ambient temperature as carried out in Example 10.

After crystallization or slurry, the diol ester may be recovered by conventional techniques, such as filtration, and may be dried. Drying may be accelerated by reducing the pressure or elevating the temperature. The diol ester is preferably dried at about 40° C. to about 50° C. under ambient pressure.

As one of skill in the art would appreciate, any of the methods of the invention, such as use of MeO-9-BBN or DEMB, reverse addition, and crystallization of TBRE, can be combined to further reduce the level of diastereoisomer impurities. In one embodiment, the combination of reduction with MeO-9-BBN through a reverse addition of reagents and crystallization of TBRE is used.

In another embodiment, the invention encompasses a process for preparing rosuvastatin or rosuvastatin lactone or a pharmaceutically acceptable salt of rosuvastatin, comprising preparing rosuvastatin diol-ester by a process as defined in any of the embodiments referred to above, and converting the rosuvastatin diol-ester to rosuvastatin or a pharmacologically acceptable salt of rosuvastatin. The intermediate may be converted to rosuvastatin, including a pharmaceutically acceptable salt of rosuvastatin, as illustrated for TBRE in the following scheme:

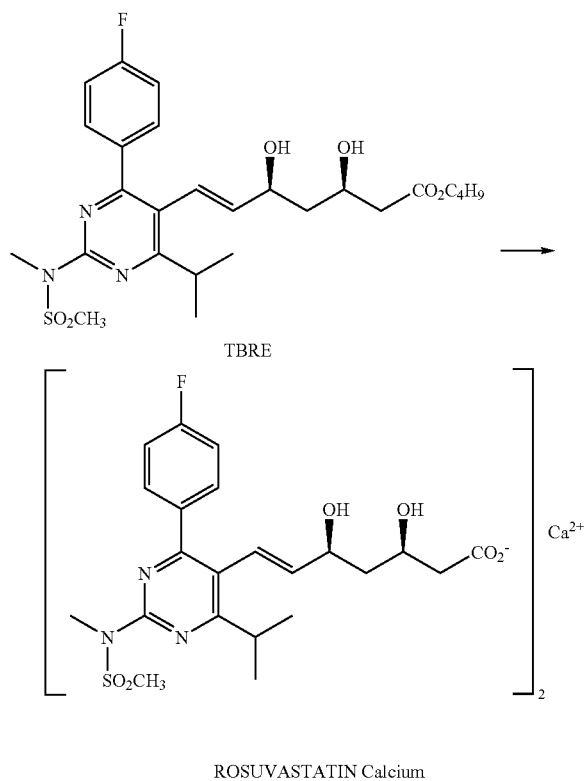

The conversion of the diol-ester to rosuvastatin or rosuvastatin lactone or a pharmaceutically acceptable salt may be performed according to US publication No. 2005/080134. The conversion may be carried out with basic hydrolysis of the ester. The basic hydrolysis of the statin diol-ester may be carried out with one or more equivalents of an alkali metal or alkaline earth metal base such as NaOH or $Ca(OH)_2$, in organic solvents such as $C_3$ to $C_8$ ethers (tetrahydrofuran, isopropyl ether), ACN (acetonitrile), $C_1$ to $C_4$ alcohols (MeOH, EtOH, IPA (isopropyl alcohol), propanol, butanol, etc.), $C_3$ to $C_8$ ketones, or $C_3$ to $C_8$ esters (acetone, methyl ethyl ketone, methyl isopropyl ketone, ethyl acetate). The hydrolysis may also be carried out with water, a mixture of the above solvents, or a mixture of water and the above solvents, preferably at room temperature or by heating. In one embodiment, the diol ester obtained is reacted with sodium or calcium hydroxide to obtain the sodium or calcium salt. In another embodiment, the diol ester is reacted with sodium hydroxide followed by conversion the to the calcium salt. A source of calcium such as calcium chloride or calcium acetate may be used for such conversion.

The rosuvastatin calcium obtained from the diastereomerically pure TBRE is also diastereomerically pure. Thus, another embodiment of the invention provides rosuvastatin, rosuvastatin lactone and salts thereof having low levels of diastereomeric impurities. One embodiment of the invention provides rosuvastatin rosuvastatin lactone and salts thereof having less than about 0.2% of diastereomeric impurities, more preferably less than about 0.15%, and even more preferably, less than about 0.1%, as measured by area percentage HPLC.

The invention further encompasses a pharmaceutical composition comprising rosuvastatin salt of the present invention, and at least one pharmaceutically acceptable excipient. Preferably, the pharmaceutical compositions comprise rosuvastatin and salts thereof having less than about 0.2% of diastereomeric impurities, more preferably less than about 0.15%, and even more preferably, less than about 0.1%, as measured by area percentage HPLC.

The invention further encompasses a process for preparing a pharmaceutical composition comprising combining rosuvastatin salt of the present invention, with at least one pharmaceutically acceptable excipient.

The invention also provides a pharmaceutical composition comprising rosuvastatin or a pharmaceutically acceptable salt thereof prepared by converting TBRE having less than about 0.3% of diastereomeric impurities, as measured by area percentage HPLC, to rosuvastatin or a pharmaceutically acceptable salt thereof, and combining the rosuvastatin with a pharmaceutically acceptable excipient.

Pharmaceutical compositions may be prepared as medicaments to be administered orally, parenterally, rectally, transdermally, bucally, or nasally. The pharmaceutical compositions of the present invention preferably Suitable forms for oral administration include tablets, compressed or coated pills, dragees, sachets, hard or gelatin capsules, sub-lingual tablets, syrups and suspensions. Suitable forms of parenteral administration include an aqueous or non-aqueous solution or emulsion, while for rectal administration suitable forms for administration include suppositories with hydrophilic or hydrophobic vehicle. For topical administration the invention provides suitable transdermal delivery systems known in the art, and for nasal delivery there are provided suitable aerosol delivery systems known in the art.

In addition to the active ingredient(s), the pharmaceutical compositions of the invention contain one or more excipients or adjuvants. Selection of excipients and the amounts to use may be readily determined by the formulation scientist based upon experience and consideration of standard procedures and reference works in the field.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the invention, nateglinide and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the invention, a liquid composition may also contain a buffer such as guconic acid, lactic acid, citric acid or acetic acid, sodium guconate, sodium lactate, sodium citrate or sodium acetate.

Selection of excipients and the amounts used may be readily determined by the formulation scientist based upon experience and consideration of standard procedures and reference works in the field.

The solid compositions of the invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the invention may comprise any of the aforementioned blends and granulates that were described with reference to tableting, however, they are not subjected to a final tableting step.

A preferred dosage is from about 5 mg to about 80 mg per day, more preferably about 5 mg to about 40 mg per day, with 5 mg, 10 mg, 20 mg, 40 mg and 80 mg tablets once a day being a preferred method of administration. These tablets may have the following inactive ingredients: microcrystalline cellulose NF, lactose monohydrate NF, tribasic calcium phosphate NF, crospovidone NF, magnesium stearate NF, hypromellose NF, triacetin NF and titanium dioxide USP.

Also provided is a method of treating a mammal in need of inhibition of the 3-hydroxy-3-methyl-glutaryl-coenzyme A ("HMG-CoA") reductase enzyme comprising administering a pharmaceutical composition prepared from TBRE having less than about 0.3% of diastereomeric impurities to the mammal.

EXAMPLES

| HPLC method for diastereomer content in Tert-Butyl ester of Rosuvastatin | |
|---|---|
| HPLC conditions: | |
| Column - | BDS Hypersil C18 |
| Mobile phase - | Gradient of Buffer and Organic modifier |
| Buffer - | Ammonium acetate buffer |
| Organic modifier - | Acetonitrile and Ethanol |
| Detection - | UV-245 nm |
| Injection - | 10 µl |
| Column temperature - | 5° C. |
| Diluent - | Acetonitrile/Water |
| Sample Preparation: | |
| 0.5 mg/ml in diluent | |
| Calculations: | |

$$\% \ 3R, 5R - \text{isomer} = \frac{\text{Area } 3R, 5R - \text{isomer in smp.} \times 100\%}{\Sigma \text{ all Areas}}$$

| HPLC method for diastereomer content in Rosuvastatin Ca | |
|---|---|
| HPLC conditions: | |
| Column - | C18 |
| Mobile phase - | Gradient of Buffer and Organic modifier |
| Buffer - | Ammonium acetate buffer |
| Organic modifier - | Acetonitrile and Ethanol |
| Detection - | UV-243 nm |
| Injection - | 10 µl |
| Column temperature - | 20° C. |
| Diluent - | Acetonitrile/Buffer |
| Sample preparation: | |
| 0.2 mg/ml in diluent | |
| Calculations: | |

$$\% \ 3R, 5R - \text{isomer} = \frac{\text{Area } 3R, 5R - \text{isomer in smp.} \times 100\%}{\Sigma \text{ all Areas}}$$

Reduction of TB-21 to TBRE (Examples 1-5)

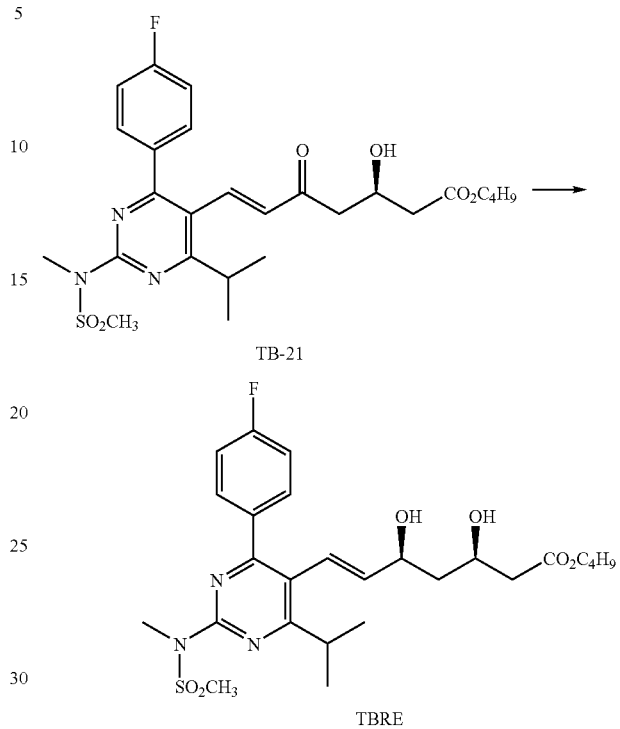

Example 1

Reverse Addition with DEMB According to U.S. Pat. No. 5,189,164

A 25 ml flask equipped with nitrogen bubbler and a magnetic stirrer was charged with TB21 (1.0 g), tetrahydrofuran (0.35 ml) and methanol (0.1 ml), forming a suspension. The suspension was stirred at room temperature to obtain a clear solution.

A 50 ml 3 necked flask equipped with a mechanical stirrer and a nitrogen bubbler was charged with tetrahydrofuran (4.4 ml) and methanol (1.2 ml), and cooled to −78° C. $NaBH_4$ (0.192 g) was added, followed by diethylmethoxyborane (2.05 ml, 1M in THF), to form a mixture that was stirred at −78° C. for 10 minutes.

The solution of TB-21 was added to the mixture of $NaBH_4$ and diethylmethoxyborane via a syringe over a period of about 1.5 hours, forming a reaction mixture. The reaction mixture was stirred at −78° C. for 30 minutes. $H_2O_2$ (0.8 ml, 30%) was added and the reaction mixture was allowed to reach room temperature, and was then evaporated to dryness to obtain a residue.

Ethyl acetate (5 ml) was added to the residue, and it washed with water (5 ml) and NaCl sat. (3.5 ml). The organic phase was separated, and further washed and separated 3 times each with $NaHCO_3$, $Na_2SO_3$ and NaCl (4 ml×3). The organic phase was then evaporated to dryness to obtain an oily residue of TBRE (1.05 g, 26.7%). Diastereoisomer content is 8.89%.

Example 2

Reverse Addition with DEMB in 60 Volumes Solvent

A 50 ml flask equipped with nitrogen bubbler and a magnetic stirrer was charged with TB-21 (1.0 g), tetrahydrofuran (3.5 ml) and methanol (1.0 ml). The suspension was stirred at room temperature to obtain a clear solution.

A 50 ml 3 necked flask equipped with a mechanical stirrer and a nitrogen bubbler was charged with tetrahydrofuran (44.0 ml) and methanol (12.0 ml) to obtain a mixture. The mixture was cooled to $-78°$ C., and $NaBH_4$ (0.192 g) was added, followed by diethylmethoxyborane (2.05 ml, 1M in THF). The mixture was stirred at $-78°$ C. for 10 minutes.

The TB-21 solution was added to the mixture via a syringe over 1.5 hours, forming a reaction mixture, and then the reaction mixture was stirred at $-78°$ C. for 30 minutes. $H_2O_2$ (0.8 ml, 30%) was added and the reaction mixture was allowed to reach room temperature. The reaction mixture was evaporated to dryness to obtain a residue.

Ethyl acetate (5 ml) was added to the residue and it washed with water (5 ml) and NaCl sat. (3.5 ml). The organic phase was separated, and further washed and separated 3 times each with $NaHCO_3$, $Na_2SO_3$ and NaCl (4 ml×3). The organic phase was then evaporated to dryness to obtain an oily residue of TBRE (1.06 g, 90.1%). Diastereoisomer content is 0.76%.

Example 3

Reduction with DEMB, Normal Addition

A 100 ml 3-necked flask equipped with a mechanical stirrer, rubber septum and nitrogen bubbler was charged with TB-21 (1.0 g), THF (47 mL) and methanol (13.5 mL) to obtain a mixture. The mixture was stirred at room temperature until the TB-21 was dissolved. The resulting solution was then cooled to $-78°$ C.

Diethylmethoxyborane (1M in THF, 2.80 mL) was added to the solution via a syringe and the solution was further stirred for 30 minutes at $-78°$ C. $NaBH_4$ (0.106 g) was added to the solution, forming a reaction mixture which was stirred for 3 hours at $-78°$ C. $H_2O_2$ (0.8 mL, 30% in water) was added at $-78°$ C. The reaction mixture was allowed to reach room temperature and was evaporated to dryness to obtain a residue.

Ethyl acetate (5 mL), water (5 mL) and NaCl saturated (3.5 mL) were added to the residue, and the organic phase was separated and further washed with $NaHCO_3$ saturated (4 mL), $Na_2SO_3$ saturated (4 mL), and NaCl saturated (4 mL). The combined organic layers were concentrated under reduced pressure to obtain a residue of the diol TBRE. (1.08 g, 81.6%). Diastereoisomer content is 0.64%.

Example 4

Reverse Addition with MeO-9-BBN

A 100 ml flask equipped with nitrogen bubbler and a magnetic stirrer was charged with TB-ROSU-21 (5.0 g), tetrahydrofuran (17.5 ml) and methanol (5 ml). The suspension was stirred at room temperature to obtain a clear solution.

A 250 ml 3 necked flask equipped with a mechanical stirrer and a nitrogen bubbler was charged with tetrahydrofuran (100 ml) and methanol (29 ml), forming a mixture. The mixture was cooled to $-78°$ C. $NaBH_4$ (1.0 g) was added followed by Methoxy-9-BBN (11.2 ml, 1M in hexanes), and the mixture was stirred at $-78°$ C. for 10 minutes.

The TB-21 solution was added to the mixture of Methoxy-9-BBN and $NaBH_4$ via a syringe a rate of 2 ml per 5 minutes, forming a reaction mixture. The reaction mixture was stirred at $-78°$ C. for 30 minutes. $H_2O_2$ (4 ml, 30%) was then added and the reaction mixture was allowed to reach room temperature. The reaction mixture was then evaporated to dryness to obtain a residue.

Ethyl acetate (25 ml) was added to the residue and it washed with water (25 ml) and NaCl sat. (17 ml). The organic phase was separated, and further washed and separated 3 times each with $NaHCO_3$, $Na_2SO_3$ and NaCl (20 ml×3). The organic phase was then evaporated to dryness to obtain an oily residue of TBRE (4.57 g, 91.1%). Diastereoisomer content is 0.11%.

Example 5

Reverse Addition with MeO-9-BBN

A 500 mL flask equipped with nitrogen bubbler and a magnetic stirrer was charged with TB-21 (50.0 g), tetrahydrofuran (175 ml), and methanol (50 ml). The suspension was stirred at room temperature to obtain a clear solution.

A 2 L, 3 necked flask equipped with a mechanical stirrer and a nitrogen bubbler was charged with tetrahydrofuran (1000 ml) and methanol (290 ml) to form a mixture. The mixture was cooled to $-78°$ C. $NaBH_4$ (10.0 g) was added followed by Methoxy-9-BBN (107 ml, 1M in hexanes), and the mixture was stirred at $-78°$ C. for 10 minutes.

The TB-21 solution was added to the mixture via a dropping funnel over 2 hours to obtain a reaction mixture. The reaction mixture was stirred at $-78°$ C. for 1 hour. $H_2O_2$ (40 ml, 30%) was then added and the reaction mixture was allowed to reach room temperature. The reaction mixture was then evaporated to dryness to obtain a residue.

Ethyl acetate (250 ml) was added to the residue and it washed with water (400 ml) and NaCl sat. (170 ml). The organic phase was separated, and further washed and separated 3 times each with $NaHCO_3$, $Na_2SO_3$ and NaCl (200 ml×3). The organic phase was then evaporated to dryness to obtain an oily residue of TBRE (42.1 g, 83.9%). Diastereoisomer content is 0.13%.

Example 6

Work Up with $NH_4Cl$

A 500 ml flask equipped with nitrogen bubbler and a mechanical stirrer was charged with TB-21 (18.60 g, assay=62.9%), tetrahydrofuran (40.5 ml) and methanol (11.5 ml). The suspension was stirred at room temperature to obtain a clear solution.

A 1000 ml 3 necked flask equipped with a mechanical stirrer and a nitrogen bubbler was charged with tetrahydrofuran (232 ml) and methanol (66.5 ml), forming a mixture. The mixture was cooled to $-78°$ C. $NaBH_4$ (2.22 g, 2.7 eq.) was added followed by Methoxy-9-BBN (24 ml, 1.1 eq., 1M in hexanes), and the mixture was stirred at $-78°$ C. for 10 minutes.

The TB-21 solution was added dropwise to the Methoxy-9-BBN mixture over 1.5 hours, forming a reaction mixture, and the reaction mixture was left for further stirring at $-78°$ C. for 1 hour. $H_2O_2$ (9.3 ml, 30%) was then added and the reaction mixture was allowed to reach room temperature.

Ethyl acetate (58 ml) and $NH_4Cl$ (174 ml) were slowly added to the reaction mixture under stirring at room temperature. The phases were filtered and separated. The organic phase washed and separated each time with $Na_2SO_3$ sat. (46 ml), then with $H_2O$ (116 ml)+NaCl sat. (116 ml), then with $H_2O$ (116 ml)+NaCl sat. (23 ml), and finally with NaCl sat. (58 ml). The organic phase was then evaporated to dryness to obtain an oily residue of TB-22 (19.02 g, 99.7%). Diastereoisomer content is 0.17%.

Example 7

Reduction in $CH_2Cl_2$

A 100 ml 3-necked flask equipped with a mechanical stirrer, rubber septum and nitrogen bubbler was charged with TB-21 (1.0 g), $CH_2Cl_2$ (47 mL) and methanol (13.5 mL). The resulting mixture was stirred at room temperature until the TB-21 was dissolved to obtain a solution. The solution was then cooled to −78° C.

Diethylmethoxyborane (1M in THF, 2.80 mL) was added to the solution via a syringe and the solution was stirred for 30 minutes at −78° C. $NaBH_4$ (0.106 g) was added, forming a reaction mixture that was stirred for 3 hours at −78° C. $H_2O_2$ (0.8 mL, 30% in water) was added. The reaction mixture was then allowed to reach room temperature and evaporated to dryness to obtain a residue.

Ethyl acetate (5 mL), water (5 mL) and NaCl saturated (3.5 mL) were added to the residue. The organic phase was separated and further washed with $NaHCO_3$ saturated (4 mL), $Na_2SO_3$ saturated (4 mL) and NaCl saturated (4 mL). The combined organic layers were concentrated under reduced pressure to obtain a residue of the diol TBRE (1.15 g, 83.6%). Diastereoisomer content is 7.5%.

Example 8

Reduction in Toluene

A 100 ml 3-necked flask equipped with a mechanical stirrer, rubber septum and nitrogen bubbler was charged with TB-21 (1.0 g), toluene (47 mL) and methanol (13.5 mL). The resulting mixture was stirred at room temperature until the TB-21 was dissolved to obtain a solution. The solution was then cooled to −78° C.

Diethylmethoxyborane (1M in THF, 2.80 mL) was added to the solution via a syringe and the solution was stirred for 30 minutes at −78° C. $NaBH_4$ (0.106 g) was added, forming a reaction mixture that was stirred for 3 hours at −78° C. $H_2O_2$ (0.8 mL, 30% in water) was added at −78° C. The reaction mixture was then allowed to reach room temperature and evaporated to dryness to obtain a residue.

Ethyl acetate (5 mL), water (5 mL) and NaCl saturated (3.5 mL) were added to the residue. The organic phase was separated and further washed with $NaHCO_3$ saturated (4 mL), $Na_2SO_3$ saturated (4 mL) and NaCl saturated (4 mL). The combined organic layers were concentrated under reduced pressure to obtain a residue of the diol TBRE. (1.19 g, 80.3%). Diastereoisomer content is 11.7%

Crystallization Examples (Examples 9-21)

| Example | Level of diastereoisomers in starting material (% area by HPLC) | Level of diastereoisomers after crystallization (% area by HPLC) |
|---|---|---|
| 9  | 1.1  | 0.52 |
| 10 | 1.1  | 0.51 |
| 11 | 1.1  | 0.62 |
| 12 | 1.1  | 0.55 |
| 13 | 1.1  | 0.50 |
| 14 | 0.79 | 0.38 |
| 15 | 0.79 | 0.43 |
| 16 | 0.79 | 0.43 |
| 17 | 0.79 | 0.42 |
| 18 | 0.79 | 0.42 |
| 19 | 0.79 | 0.34 |
| 20 | 1.1  | 0.47 |
| 21 | 0.23 | 0.08 |

Example 9

Crystallization of TBRE in MeOH

TBRE (1 g, 1.1% diastereoisomers) was dissolved in MeOH (5 ml) under heating. The solution was then allowed to cool to room temperature, and was stirred at this temperature overnight. The solid was then filtered under reduced pressure, washed, and dried at 45° C. under atmospheric pressure for 18 hrs to obtain TBRE (0.52% diastereoisomers).

Example 10

Slurry TBRE in MeOH

TBRE (1 g, 1.1% of diastereoisomers) was suspended in MeOH (5 ml) while stirring at ambient temperature overnight. The solid was then filtered under reduced pressure, washed, and dried at 45° C. under atmospheric pressure for 18 hrs to obtain 0.60 g of TBRE (diastereoisomers 0.51%)

Example 11

Crystallization of TBRE from 2 ml PGME

TBRE (1 g, 1.1% diastereoisomers) was dissolved in PGME (2 ml) by heating to 100° C. The solution was then allowed to cool to room temperature, and was stirred at this temperature overnight. The solid was then filtered under reduced pressure, washed, and dried at 45° C. under atmospheric pressure for 18 hrs to obtain 0.67 g of TBRE (0.62% diastereoisomers).

Example 12

Crystallization of TBRE from $ACN:H_2O$

TBRE (1 g, 1.1% diastereoisomers) was dissolved in a mixture of 5.5 ml ACN and 4 ml $H_2O$ by heating to reflux. The solution was allowed to cool to room temperature, and was stirred at this temperature for 72 hrs. The solid was then filtered under reduced pressure, washed, and dried at 45° C. under atmospheric pressure for 18 hrs to get 0.84 g of TBRE (0.55% diastereoisomers).

Example 13

Crystallization of TBRE from Acetone:$H_2O$ (6:2)

TBRE (1 g, 1.1% diastereoisomers) was dissolved in a mixture of 6 ml acetone and 2 ml $H_2O$ by heating to reflux. The solution was allowed to cool to room temperature, and was stirred at this temperature overnight. The solid was then filtered under reduced pressure, washed, and dried at 45° C. under atmospheric pressure for 18 hrs to get 0.68 g of TBRE (0.50% diastereoisomers).

Example 14

Crystallization of TBRE from Acetone:MTBE

TBRE (1 g, 0.79% diastereoisomers) was dissolved in a mixture of 2 ml acetone and 10 ml MTBE by heating to reflux. The solution was then allowed to cool to room temperature, and was stirred at this temperature overnight. The solid was then filtered under reduced pressure, washed, and dried at 45°

C. under atmospheric pressure for 18 hrs to get 0.46 g of TBRE (0.38% diastereoisomers).

Example 15

Crystallization of TBRE from MeOH:H$_2$O (5:0.5)

TBRE (1 g, 0.79% diastereoisomers) was dissolved in a mixture of 5 ml MeOH and 0.5 ml H$_2$O by heating to reflux. The solution was then allowed to cool to room temperature, and was stirred at this temperature overnight. The solid was then filtered under reduced pressure, washed and dried at 45° C. under atmospheric pressure for 18 hrs to get 0.84 g of TBRE (0.43% diastereoisomers).

Example 16

Crystallization of TBRE from EtOH:H$_2$O (5:0.5)

TBRE (1 g, 0.79% diastereoisomers) was dissolved in a mixture of 5 ml EtOH and 0.5 ml H$_2$O by heating to reflux. The solution was then allowed to cool to room temperature, and was stirred at this temperature overnight. The solid was then filtered under reduced pressure, washed, and dried at 45° C. under atmospheric pressure for 18 hrs to get 0.77 g of TBRE (0.43% diastereoisomers).

Example 17

Crystallization of TBRE from EtOH:MTBE

TBRE (1 g, 0.79% diastereoisomers) was dissolved in a mixture of 2 ml EtOH and 10 ml MTBE by heating to reflux. The solution was then allowed to cool to room temperature, and was stirred at this temperature overnight. The solid was then filtered under reduced pressure, washed, and dried at 45° C. under atmospheric pressure for 18 hrs to get 0.55 g of TBRE (0.42% diastereoisomers).

Example 18

Crystallization of TBRE from ACN:MTBE

TBRE (1 g, 0.79% diastereoisomers) was dissolved in a mixture of 0.5 ml ACN and 10 ml MTBE by heating to reflux. The solution was allowed to cool to room temperature. The mixture was stirred at this temperature overnight. The solid was then filtered under reduced pressure, washed and dried at 45° C. under atmospheric pressure for 18 hrs to get 0.61 g of TBRE (0.42% diastereoisomers).

Example 19

Crystallization of TBRE from MeOH:MTBE

TBRE (1 g, 0.79% diastereoisomers) was dissolved in a mixture of 0.5 ml MeOH and 10 ml MTBE by heating to reflux. The solution was allowed to cool to room temperature, and was stirred at this temperature overnight. The solid was then filtered under reduced pressure, washed, and dried at 45° C. under atmospheric pressure for 18 hrs to get 0.61 g of TBRE (0.34% diastereoisomers).

Example 20

Crystallization of TBRE from MEK:MTBE

TBRE (1 g, 1.1% diastereoisomers) was dissolved in 2 ml MEK at reflux temperature. MTBE (6 ml) was added at this temperature. No precipitation was observed. The solution was allowed to cool to room temperature and an additional amount of MTBE (10 ml) was added. The addition of MTBE did not induce any precipitation. After being stirred at ambient temperature for 72 hrs, a precipitation was observed. The solid was filtered under reduced pressure, washed, and dried at 45° C. under atmospheric pressure for 18 hrs to get 0.62 g of TBRE (0.47% diastereoisomers).

Example 21

Crystallization of TBRE from Toluene

TBRE (2 g, 0.23% diastereoisomers) was dissolved in Toluene (7 ml) by heating to approximately 60° C. The solution was then allowed to cool to room temperature, and was cooled afterwards in an ice bath to 0° C. The resulting mixture was stirred at this temperature overnight. The solid was then filtered under reduced pressure, washed, and dried at 50° C. under reduced pressure for 18 hrs to get 1.59 g of TBRE (0.08% diastereoisomers).

Example 22

Rosuvastatin Calcium with Diastereomers Less than 0.1%

A 25 ml flask equipped with a mechanical stirrer was charged with EtOH (6 mL) water (3.6 ml), and TBRE (1.2 g, 0.19% diastereoisomers). To this suspension, NaOH 47% 1.2 eq (0.23 g) was added dropwise at 25±5° C. The resulting mixture was stirred at 25±5° C. for three hours. The mixture was carefully acidified to pH=10 by addition of 0.01N HCl and then washed with toluene (6 mL). The aqueous layer was isolated and concentrated under reduced pressure at 40° C. to about ⅔ of an initial volume.

Example 23

Preparation of Rosuvastatin Calcium from Rosuvastatin Ester

A 1000 ml reactor equipped with a mechanical stirrer was charged with EtOH (100 mL) water (60 ml) t-Butyl-Rosuvastatin (20 g) and NaBH$_4$ (0.1 g). To this suspension, NaOH 47% 1.1 eq (3.5 g) was added dropwise at 25±5° C. and the mixture was stirred at 25±5° C. for two hours. The mixture was then filtered under reduced pressure with a Sinter to eliminate the active carbon present in the solution.

To this suspension water (140 ml) was added and the reaction mixture was acidified with HCl 0.1M until PH 8-10. The mixture was then washed with Toluene (100 ml) and stirred at 25±5° C. for half an hour. The aqueous layer was isolated. To the aqueous phase active carbon was added and the suspension was stirred at 25±5° C. for 30 min. The mixture was filtered under reduced pressure with Sinter and Hyflo to eliminate the active carbon present in the solution. Thereafter the reaction mixture was concentrated under reduced pressure at 40° C. to half the solution volume. Make-up of the solution was performed to 10 volumes of water versus TBRE. The solution was heated to 40-45° C. CaCl$_2$ (4.13 g) was added dropwise to this solution over 30-90 min at 38-45° C. The suspension was then cooled to 25±5° C., stirred at 25±5° C. for 1 hr, filtered and washed with water (4×20 ml) to get a powdery compound (17.3 g dry, 92%).

The resulting solution was placed in a flask and heated to 40° C. Solid CaCl$_2$ (0.25 g) was added portionwise to this solution while stirring. The resulting mixture was then cooled to 25±5° C., stirred at 25±5° C. for 1 hr, filtered and washed with water to get a powdery product, which was dried in vacuum at 50° C.

Having thus described the invention with reference to particular preferred embodiments and illustrated it with Examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. All references mentioned herein are incorporated in their entirety.

What is claimed is:

1. A one pot process for preparing rosuvastatin or a pharmaceutically acceptable salt thereof comprising:
   a) combining MeO-9-BBN with an organic solvent and a source of hydride ions;
   b) adding to said combination a solution of a rosuvastatin intermediate keto-ester in an organic solvent, wherein the rosuvastatin intermediate keto-ester has the following formula:

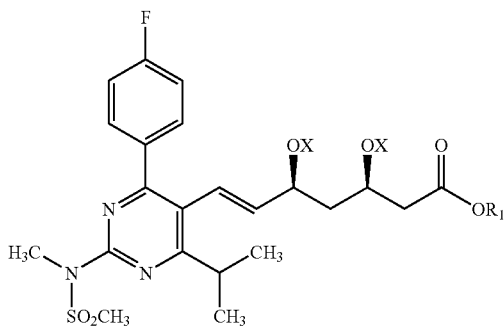

wherein X is hydrogen or forms a double bond to provide a ketone, with the proviso that at least one X forms a double bond, and $R_1$ is a carboxy protecting group, to obtain a reaction mixture;
   c) maintaining the reaction mixture to reduce the intermediate; and
   d) hydrolyzing the reduced intermediate to rosuvastatin or a pharmaceutically acceptable salt thereof.

2. The process of claim 1, wherein the organic solvent is selected from the group consisting of non-polar hydrocarbon solvent, chlorinated solvent, $C_1$ to $C_4$ alcohol, non-protic solvent, $C_2$ to $C_8$ ether, and mixtures thereof.

3. The process of claim 2, wherein the organic solvent is selected from a group consisting of methylene chloride, toluene, methyl t-butyl ether, di-ethyl ether, tetrahydrofuran, dioxane, methanol, ethanol, isopropanol, and n-butanol.

4. The process of claim 3 wherein the organic solvent is a mixture of methanol and THF.

5. The process of claim 4, wherein the ratio of THF/MeOH is about 3.5/1 by volume (per gram of the ester).

6. The process of claim 1, wherein the reaction mixture contains about 1.5 to about 4 equivalents of hydride ion per gram of rosuvastatin keto-ester.

7. The process of claim 1, wherein the source of hydride ions is selected from a group consisting of sodium borohydride, potassium borohydride, lithium borohydride, selectride and sodium triacetoxy borohydride.

8. The process of claim 7, wherein the source of hydride ions is sodium borohydride.

9. The process of claim 1, wherein the keto-ester is added drop-wise.

10. The process of claim 1, wherein the keto-ester is added over a period of at least about thirty minutes.

11. The process of claim 1 wherein the reaction mixture has a total amount of solvent from the keto ester-solution and solvent that is combined with the Methoxy-9-BBN of about 30 to about 80 volumes (ml per gram of keto ester).

12. The process of claim 1, wherein the source of hydride ions is present in an amount of about 1.5 to about 4 equivalents (per gram of keto ester).

13. The process of claim 12, wherein the source of hydride ions is present in an amount of about 2.7 equivalents (per gram of keto ester).

14. The process of claim 1, wherein the reaction mixture is maintained for at least about 5 minutes.

15. The process of claim 14, wherein the reaction mixture is maintained for about 0.5-3 hours.

16. The process of claim 1, wherein the process further comprises cooling the combination containing the hydride ions to a temperature of about −70° C. to about −80° C.

17. The process of claim 16, wherein cooling is to a temperature of about −70° C.

18. The process of claim 1, wherein the process further comprises quenching the reaction mixture.

19. The process of claim 18, wherein quenching comprises combining the reaction mixture with a quenching agent selected from a group consisting of hydrogen peroxide, 3-chloroperbenzoic acid, ammonium chloride, aqueous solution of HCl, acetic acid, oxone, sodium hypochlorite, dimethyl disulfide, diethanolamine, acetone and hydroxylamine-O-sulfonic acid.

20. The process of claim 19, wherein the quenching agent is hydrogen peroxide.

* * * * *

UNITED STATES PATENT AND TRADEMARK OFFICE
CERTIFICATE OF CORRECTION

PATENT NO. : 7,582,759 B2
APPLICATION NO. : 11/520296
DATED : September 1, 2009
INVENTOR(S) : Valerie Niddam-Hildesheim et al.

It is certified that error appears in the above-identified patent and that said Letters Patent is hereby corrected as shown below:

Column 24, line 21, change "Methoxy-9-BBN" to --methoxy-9-BBN--

Signed and Sealed this

Eighteenth Day of May, 2010

David J. Kappos
*Director of the United States Patent and Trademark Office*